United States Patent [19]

Casey

[11] Patent Number: 5,002,552
[45] Date of Patent: Mar. 26, 1991

[54] SURGICAL CLIP

[76] Inventor: Donn Casey, 141 Newmarket Rd., Cambridge, United Kingdom, CB5 8HA

[21] Appl. No.: 268,019

[22] Filed: Nov. 7, 1988

[30] Foreign Application Priority Data

Nov. 10, 1987 [GB] United Kingdom ............. 8726301

[51] Int. Cl.$^5$ .............................................. A61B 17/00
[52] U.S. Cl. ..................................... 606/157; 606/135; 251/9
[58] Field of Search ................. 128/325, 326, 346; 24/543, 511, 460–462; 227/DIG. 1; 606/120, 139, 140, 142, 143, 157, 158, 151, 136; 251/9

[56] References Cited

U.S. PATENT DOCUMENTS

| 3,171,184 | 3/1965 | Posse ........................... 251/9 |
| 3,766,925 | 10/1973 | Rubricius ................... 128/346 |
| 3,807,406 | 4/1974 | Rafferty et al. . |
| 3,882,854 | 5/1975 | Hulka et al. . |
| 3,926,195 | 12/1975 | Bleier et al. . |
| 4,020,530 | 5/1977 | Sartore . |
| 4,091,815 | 5/1978 | Larsen ...................... 128/346 |
| 4,112,951 | 9/1978 | Hulka et al. . |
| 4,188,953 | 2/1980 | Klieman et al. . |
| 4,212,303 | 7/1980 | Nolan . |
| 4,337,774 | 7/1982 | Perlin ....................... 128/346 |
| 4,346,869 | 8/1982 | MacNeill . |
| 4,394,864 | 7/1983 | Sandhaus . |
| 4,424,810 | 1/1984 | Jewusiak . |
| 4,489,725 | 12/1984 | Casey et al. .............. 128/346 |
| 4,822,348 | 4/1989 | Casey ....................... 128/325 |

FOREIGN PATENT DOCUMENTS

| 0069653.A1 | 1/1983 | European Pat. Off. . |
| 0095249.A2 | 11/1983 | European Pat. Off. . |
| 0150797.A2 | 4/1984 | European Pat. Off. . |
| 0122046.A1 | 10/1984 | European Pat. Off. . |
| 0128011.A1 | 12/1984 | European Pat. Off. . |
| 2237610 | 2/1975 | France . |
| 83/03345 | 10/1983 | PCT Int'l Appl. . |
| 0410321 | 5/1934 | United Kingdom . |
| 0651186 | 3/1951 | United Kingdom . |
| 0668771 | 3/1952 | United Kingdom . |
| 0941562 | 11/1963 | United Kingdom . |
| 1021280 | 3/1966 | United Kingdom . |
| 1124914 | 8/1968 | United Kingdom . |
| 1141389 | 1/1969 | United Kingdom . |
| 1253789 | 11/1971 | United Kingdom . |
| 1392216 | 4/1975 | United Kingdom . |
| 1530282 | 10/1978 | United Kingdom . |
| 2043157.A | 10/1980 | United Kingdom . |
| 2055953.A | 3/1981 | United Kingdom . |
| 2069848.A | 9/1981 | United Kingdom . |
| 2097851.A | 11/1982 | United Kingdom . |
| 2177748.A | 1/1987 | United Kingdom . |

Primary Examiner—C. Fred Rosenbaum
Assistant Examiner—William Lewis
Attorney, Agent, or Firm—Robert F. O'Connell

[57] ABSTRACT

A plastics clip for performing sexual sterilization comprises two jaws each having a lining of silicone rubber, hinged to move from an open position to a closed position, in which a Fallopian tube is occluded. A catch mechanism biasses the jaws apart when the clip is open, by means of pressure from a resilient finger on a cam profile attached to the upper jaw. The finger and underside of the cam profile engage when the jaws reach their closed position, and lock the jaws closed. During closure, a resilient tongue formed on the upper jaw and a projection forming a hook on the lower jaw prevent the tube from escaping. Due to the biassing, the clip will spring back open during application if not sufficiently closed to engage the catch mechanism. In conjunction with the biassing, two moulded recesses and the shaping of the clip in a region adjacent the hinge end the clip to be located firmly in an applicator before closure. When closed, the jaw members define therebetween a first region lying adjacent the hinge and receiving a tube to be occluded, and a second region at the free ends of the jaws remote from the hinge. The second region has a cross-section of a size to prevent a Fallopian tube being withdrawn therethrough while permitting the mesosalpinx of the tube to pass relatively freely.

5 Claims, 2 Drawing Sheets

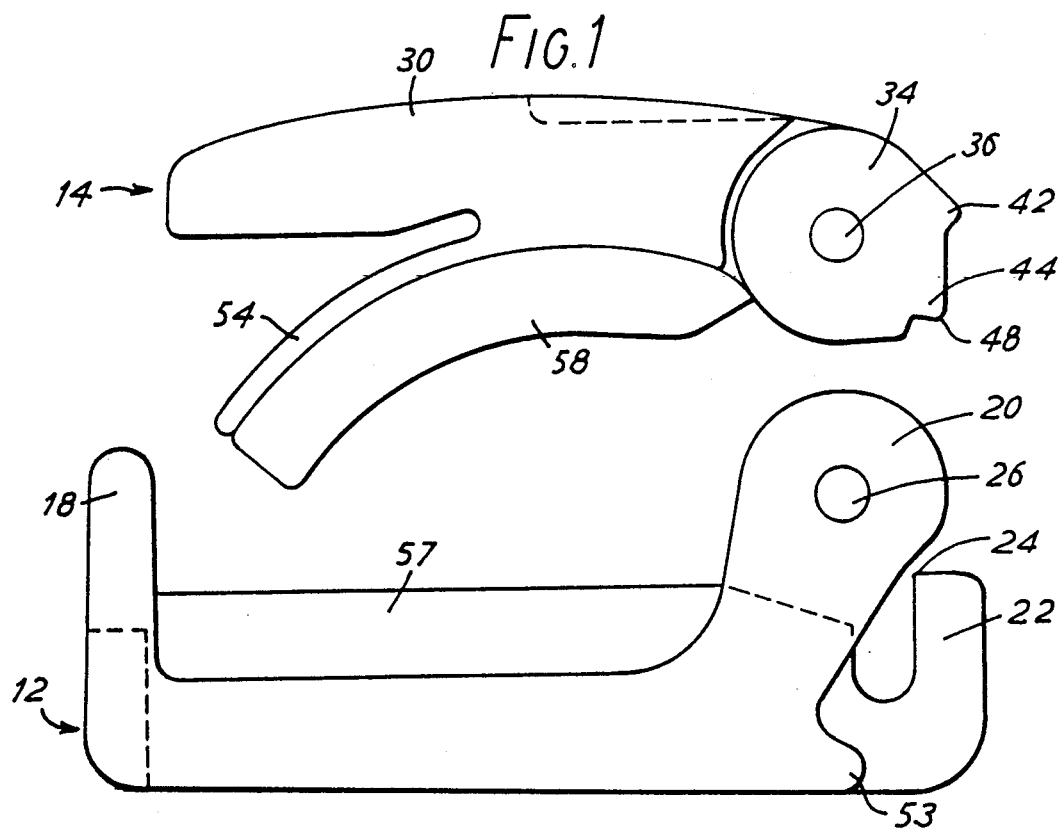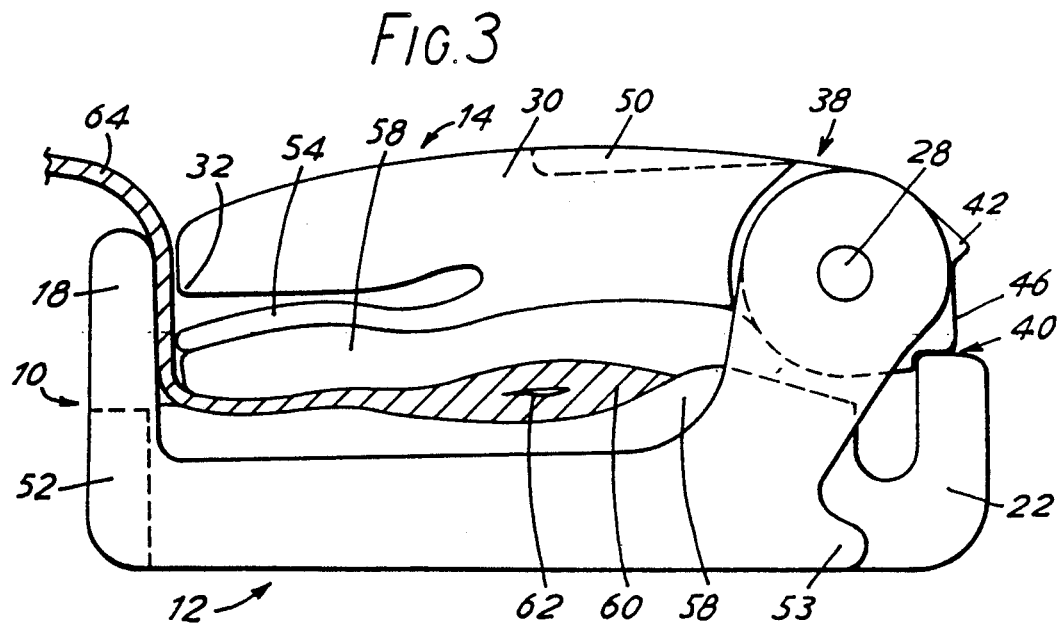

SURGICAL CLIP

FIELD OF THE INVENTION

The present invention relates to surgical clips for occluding bodily ducts, and, in particular, to clips for performing sexual sterilization, especially in females, comprising two rigid jaws hinged together to form a mouth for receiving a bodily duct to be occluded by closing the jaws.

Various clips have been proposed which incorporate catch mechanisms for holding the clips closed after application.

BRIEF SUMMARY OF THE INVENTION

In a first aspect, the invention provides a surgical clip for a surgical clip for performing sexual sterilization, comprising:

two jaw members;

hinge means pivotably connecting said jaw members such that said jaw members extend from the hinge means to free end portions defining a mouth for receiving a bodily duct to be occluded by closing said jaws; and a catch mechanism disposed adjacent said hinge means and comprising a cam profile formed on one of said jaw members and a resilient finger formed on the other of said jaw members, said resilient finger riding over said cam profile during pivoting of said jaw members relative to one another;

wherein said cam profile is so shaped that the contact force exerted by said resilient finger on said cam profile acts, during substantially the whole of a pivoting movement of said jaw members to close them, along a line which passes between the axis about which said jaw members are pivotable and one of said jaw members and wherein engagement of said resilient finger with said cam profile acts to bias said two jaw members away from one another, said surgical clip further comprising:

a discontinuity formed on said cam profile;

wherein, during pivoting of said jaw members towards one another, said resilient finger riding on said cam profile passes over said discontinuity so that the engagement of said resilient finger with said cam profile thereafter acts to oppose movement of said jaw members away from each other.

The outward bias which this arrangement ensures is desirable for a number of reasons.

Firstly, the bias serves to retain the clip securely in the jaws of an applicator during surgical application. Secondly, it is frequently the case that such clips are applied by means of laparoscopic techniques. In such circumstances, the clip must be partially closed to enable it to pass down the relatively narrow cannula tube. However, once the clip has passed through the tube, it must be re-opened fully to accommodate the duct to which it is to be applied. The strong outward bias provided by the clip of the invention ensures that the jaws spring apart as soon as the clip is clear of the cannula tube.

Furthermore, because the jaws are strongly biased apart, the clip will not stay closed unless the catch mechanism is properly engaged. Consequently, it is easy to tell whether or not the clip is properly closed because, if it is not, the jaws will simply remain sprung apart.

A number of clips are known which purport to provide the desired outward bias but it has been found that, in practice, the jaws will remain static in any of a wide range of partially-opened positions. I have appreciated that the reason for this is that the contact force between the interengaging biassing members on the two jaws acts along a line passing through the axis about which the jaws pivot. As a result, no biassing force is actually exerted on the jaws.

In a second aspect, the invention provides a surgical clip for a surgical clip for performing sexual sterilization in females, comprising:

two jaw members;

hinge means pivotably connecting said jaw members such that said jaw members extend from the hinge means to free end portions defining a mouth for receiving a bodily duct to be occluded by closing said jaws; and a catch mechanism disposed adjacent said hinge means, said catch mechanism retaining said jaw members in position relative to each other when said jaw members are closed around a bodily duct;

wherein when said jaw members are closed around a bodily duct, said jaw members define first and second regions therebetween, said first region lying adjacent said hinge means and receiving a Fallopian tube to be occluded, said second region lying at the free ends of the jaw members remote from said hinge means, said second region having a cross section of such a size as to prevent withdrawal of said Fallopian tube therethrough from between said jaw members whilst permitting passage of the mesosalpinx of said Fallopian tube therethrough.

The location of the catch mechanism in the vicinity of the hinge and not at the mouth end ensures that there is no danger of elements of the catch engaging the vulnerable mesosalpinx and causing haemorrhage. This ensures that the regions of the jaws remote from the catch which do engage the mesosalpinx may be designed primarily with a view to avoiding trauma.

BRIEF DESCRIPTION OF THE INVENTION

A clip according to the invention will now be described in detail, by way of example, with reference to the accompanying drawings in which:

FIG. 1 is an exploded view of a clip according to the invention;

FIG. 3 shows the clip with its jaws closed around a Fallopian tube.

DETAILED DESCRIPTION OF A PREFERRED EMBODIMENT

Figure 2:
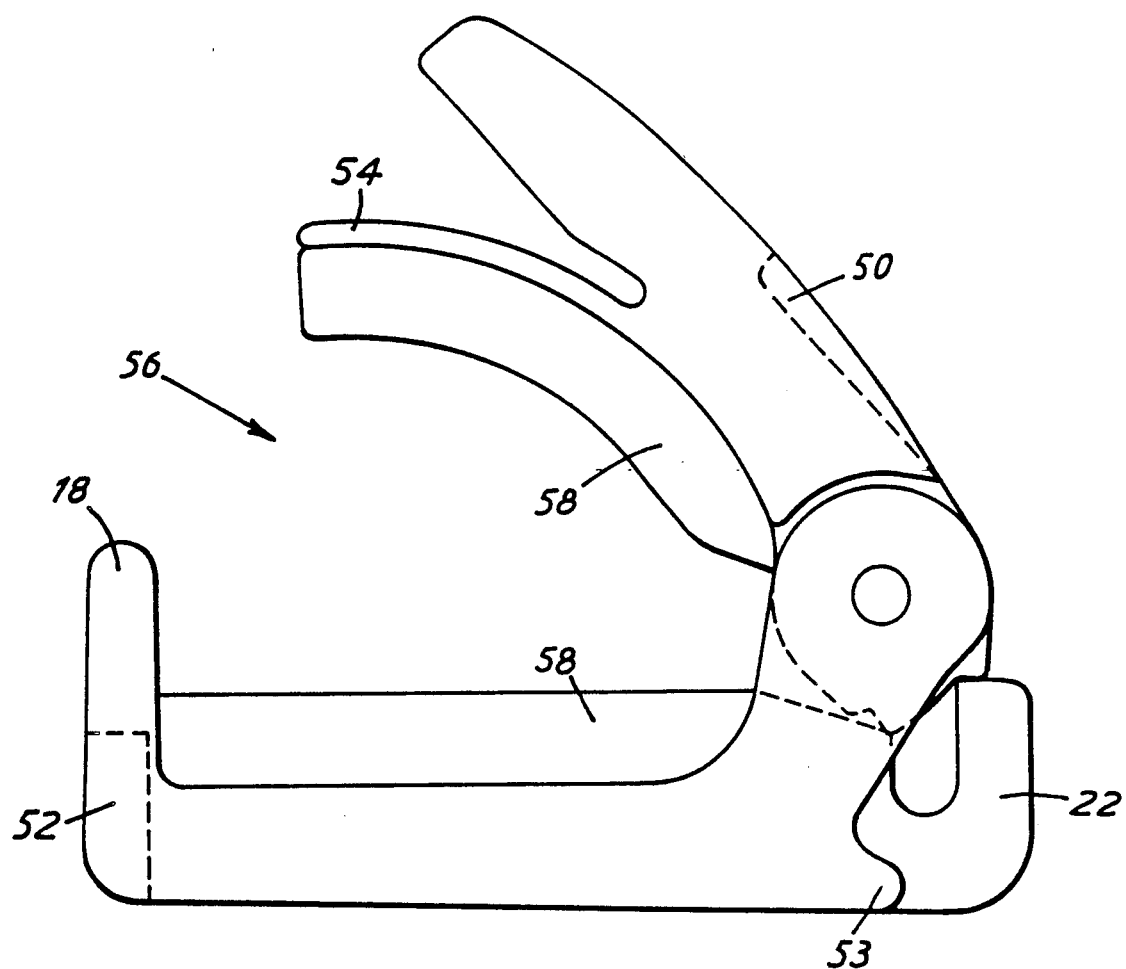
FIG. 2 shows the two jaws of the clip of FIG. 1 in an open position.

FIGS. 1 to 3 show a surgical clip 10 for performing sexual sterilization, comprising upper and lower jaws 14, 12 connected at one end by a hinge 38 and movable between an open position (FIG. 2). in which a Fallopian tube 60 may be introduced between the jaws, and a closed position (FIG. 3) in which the tube is trapped between the jaws and occluded by them.

The jaws are shown separated in FIG. 1. The lower jaw 12 comprises a rigid shank 16 having a generally perpendicular extension forming a hook 18 at one end, and at the other end two generally disc-like extensions 20 and a resilient finger 22 at the other. The centres of the disc-like extensions 20 are aligned and have holes 26 formed in then which receive a pivot pin 28. The resilient finger 22 forms part of the catch and bias mechanism 40 to be described.

The upper jaw 14 also comprises a rigid shank 30 of such length that, when the clip 10 is closed, a narrow channel is formed between the free end 32 of the upper jaw 14 and the hook or extension 18 on the lower jaw 12. The under side of the upper jaw 14 has a resilient tongue 54 formed of a thin strip of resilient material which is integral at one end with the shank 30 and free at the other. The tongue 54 is so shaped that, when the clip 10 is in the open position, the free portion of the tongue 54 curves away from the shank 30. Each jaw has a resilient lining 58 of, for example, silicone rubber moulded upon it. On the upper jaw 14, the lining 58 is carried by the resilient tongue 54.

At the other end of the upper jaw 14 is a single disc-like extension 34 provided with a hole 36 for receiving the pivot pin 28.

In the assembled clip 10, the disc 34 lies between the discs 20 with the pivot pin 28 located in the holes 26, 36 to allow the disc 34 to rotate relative to the discs 20 while restricting lateral movement of the jaws.

The circumferential surface of the disc 34 forms part of the catch and bias mechanism 40. The surface forms a cam profile having two discontinuities or lips separated by an inclined ramp. The inclined ramp 46 is such that the radial distance of the surface from the pivot pin 28 increases smoothly. At its outermost end, the ramp surface 46 terminates in an inwardly extending radial step or lip 48. At its innermost end, the ramp surface 46 is bordered by an outwardly projecting stop surface 42.

With the clip 10 in the open position (FIG. 2), the free end 24 of the resilient finger abuts the stop surface 42 which limits opening of the clip 10.

As the clip is being closed, the finger 22 runs along the ramp surface 46 of the cam profile so that it is gradually forced outwards as the clip closes. The ramp surface 46 is shaped so that the line of force from the point of contact of the finger 22 on the ramp surface of the cam profile is offset from the pivot pin 28, that is to say, it passes between the axis of rotation of the disc 34 (the centre of pivot pin 28) and the jaw 12 at all times during closing of the clip other than the moment when the finger 22 has reached the very edge of the lip 48. Consequently, during closing the clip 10 is strongly biassed towards the open position. Prior to the free end 24 of the finger reaching the lip 48 of the cam profile, any release of closing pressure will thus cause the clip to spring back to the fully open position (FIG. 2). The ramp surface 46 of the cam profile is also contoured to provide greater opening bias by deflecting the finger 22 further from the pivot 28 as it approaches the lip 48.

Any further closing movement causes the finger 22 to move past the lip 48. Contact between the free end 24 of the finger and the ramp surface 46 ceases as the finger 22 reverts to its natural shape, moving towards the radial surface of the disc 34. The jaws 12, 14 are thus locked in the closed position (FIG. 3) as the finger 22 cannot rise over the lip 48 if attempts are made to open the clip 10.

The application of a clip 10 to occlude a single Fallopian tube will now be described with particular reference to FIGS. 2 and 3.

With the clip in the fully open position (FIG. 2) the Fallopian tube 60 and an area of the mesosalpinx 64 are placed in the mouth 56 formed between the jaws 12, 14. The tube 60 then occupies a plane generally perpendicular to the plane of the jaws 12, 14. The tube 60 is free to move in and out of the mouth 56 although the tongue 54 and the hook 18 on the lower jaw 12 partially restrict the mouth 56.

In use, the jaws 12, 14 hinge together to close the mouth 56 and trap the tube 60. At an intermediate position, the tongue 54 has approached and just reached the jaw 12 and thus, prevents the tube 60 escaping as further pressure is applied to close the clip. As the closure continues, the tongue 54 and projection 18 both restrict the movement of the tube 60 relative to the clip 10.

When the point of full closure has been reached (FIG. 3) and the jaws 12, 14 are locked in the closed position by the catch mechanism 40, the lumen 62 is fully occluded. The jaws 12, 14 exert no compressive force on the tube 60, other than the pressure from resilient linings 58 which serves to prevent recanalisation when necrosis of the muscular tissue around the tube 60 occurs.

During closure, the tongue 54 is deflected towards the upper jaw 14 and the tip of the tongue 54 approaches the hook 18. The gap between tongue 54 and hook 18 serves to prevent the escape of the tube 60 from the clip 10 whilst allowing the mesosalpinx 64 to pass undamaged between the jaws 12 and 14. It can be seen from FIG. 3 that the configuration of the tongue 54 is such that it is still slightly curved away from the jaw 14 when the clip 10 is closed. In the event of a force being applied to pull the tube 60 out of the closed clip 10, the tension on the mesosalpinx 64 would act to further deflect the tongue 54 towards the shank 30 of the upper jaw 14, reducing the gap between the tip of the tongue 54 and the hook 18 and ensuring that the tube 60 would not be able to escape.

The elongate tongue 54 also exerts a force on the other jaw 12, when the clip 10 is closed, at the end of the jaw 12 remote from the hinge 38. This helps to even out the compressive force exerted by the jaws 12 and 14, which would otherwise be greater adjacent the hinge. Consequently, the likelihood of the force being insufficient to close the Fallopian tube, even if it is positioned close to the free ends of the jaws.

The clip 10 is particularly suited for use with a laparoscope or similar application methods since, because of the opening bias of the jaws, it will automatically reopens to its fullest extent after passing through a laparoscopic cannula tube. Additionally, in conjunction with recess 50, 52 and the shaping of the clip 10 in the region 53 and adjacent its hinge end in the jaws of the clip the opening bias provided positive location of the clip 10 in the applicator.

The principal benefit is the fact that the clip 10 will spring fully open if not completely closed providing the surgeon with a clear-cut end point to the operation.

The clip described is intended to be manufactured from mouldable materials which lend themselves to mass production methods whilst at the same time having smooth surfaces and rounded edges such as to be largely atraumatic in use. Materials for the jaws, linings and pivot pin are available which satisfy all surgical requirements as to their toxicity and purity whilst still being suitable for such production methods.

I claim:

1. A surgical clip for performing sexual sterilization, comprising:
   two jaw members;
   hinge means pivotably connecting said jaw members such that said jaw members extend from the hinge means to free end portions defining a mouth for receiving a bodily duct to be occluded by closing said jaws; and a bias mechanism disposed adjacent said hinge means and comprising a cam profile formed on one of said jaw members and a resilient finger formed on the other of said jaw members, said cam profile being a substantially continuous surface intermediate first and second ends thereof, said resilient finger riding over said substantially continous surface from said first end to said second end thereof during pivoting of said jaw members relative to one another to close them;

wherein said cam profile is so shaped that the contact force exerted by said resilient finger on any part of said substantially continuous surface intermediate said first end and said second end acts along a line which is offset from the axis about which said jaw members are pivotable and passes between said axis and the other of said jaw members and wherein engagement of said resilient finger with said cam profile acts to bias said two jaw members away from one another, said surgical clip further comprising:

a discontinuity formed on said cam profile adjacent said second end thereof;

wherein, during pivoting of said jaw members towards one another, said resilient finger riding on said cam profile passes over said discontinuity so that the engagement of said resilient finger with said cam profile thereafter acts to oppose movement of said jaw members away from each other.

2. The invention set forth in claim 1, wherein said jaw members are disposed to one side of said hinge means and wherein said bias mechanism is disposed on the opposite side of said hinge means to said jaw members.

3. The invention set forth in claim 1, further comprising:

a stop formed on said cam profile adjacent said first end thereof and engageable with said resilient finger;

wherein engagement of said resilient finger with said stop limits the extent to which said jaw members can be pivoted away from one another.

4. The invention set forth in claim 1, for performing sexual sterilization in females wherein, when said jaw members are closed around a bodily duct, said jaw members define first and second regions therebetween, said first region lying adjacent said hinge means and receiving a Fallopian tube to be occluded; said second region lying at the free ends of the jaw members remote from said hinge means; said second region having a cross section of such a size as to prevent withdrawal of said Fallopian tube therethrough from between said jaw members whilst permitting passage of the mesosalpinx of said Fallopian tube therethrough.

5. A surgical clip for performing sexual sterilization in females, comprising:

two jaw members;

hinge means pivotably connecting said jaw members such that said jaw members extend from the hinge means to free end portions defining a mouth for receiving a bodily duct to be occluded by closing said jaws; and a catch mechanism disposed adjacent said hinge means, said catch mechanism retaining said jaw members in position relative to each other when said jaw members are closed around a bodily duct;

wherein when said jaw members are closed around a bodily duct, said jaw members define first and second regions therebetween, said first region lying adjacent said hinge means and receiving a Fallopian tube to be occluded, said second region lying at the free ends of the jaw members remote from said hinge means, said second region having a cross section of such a size as to prevent withdrawal of said Fallopian tube therethrough from between said jaw members whilst permitting passage of the mesosalpinx of said Fallopian tube therethrough.

* * * * *